US012678622B2

(12) United States Patent
Mikata et al.

(10) Patent No.: US 12,678,622 B2
(45) Date of Patent: Jul. 14, 2026

(54) ELECTRIC POTENTIAL THERAPY DEVICE

(71) Applicants: RAY & COMPANY INC., Omihachiman (JP); NATIONAL UNIVERSITY CORPORATION SHIGA UNIVERSITY OF MEDICAL SCIENCE, Otsu (JP)

(72) Inventors: Saburo Mikata, Omihachiman (JP); Takayoshi Abe, Omihachiman (JP); Hisakazu Ogita, Otsu (JP)

(73) Assignees: RAY & COMPANY INC., Omihachiman (JP); NATIONAL UNIVERSITY CORPORATION SHIGA UNIVERSITY OF MEDICAL SCIENCE, Otsu (JP)

( * ) Notice: Subject to any disclaimer, the term of this patent is extended or adjusted under 35 U.S.C. 154(b) by 334 days.

(21) Appl. No.: 18/276,689

(22) PCT Filed: Jan. 27, 2023

(86) PCT No.: PCT/JP2023/002592
§ 371 (c)(1),
(2) Date: Aug. 10, 2023

(87) PCT Pub. No.: WO2024/157446
PCT Pub. Date: Aug. 2, 2024

(65) Prior Publication Data
US 2025/0018188 A1 Jan. 16, 2025

(51) Int. Cl.
*A61N 1/36* (2006.01)
(52) U.S. Cl.
CPC ................................. *A61N 1/36034* (2017.08)
(58) Field of Classification Search
CPC ............ A61N 1/36034; A61N 1/36192; A61N 1/36175

(Continued)

(56) References Cited

U.S. PATENT DOCUMENTS

| | | | |
|---|---|---|---|
| 2005/0234524 A1 | 10/2005 | Horiguchi et al. | |
| 2021/0154481 A1 | 5/2021 | Scheltienne et al. | |

FOREIGN PATENT DOCUMENTS

| | | |
|---|---|---|
| JP | H08-194019 A | 7/1996 |
| JP | H10-272191 A | 10/1998 |

(Continued)

OTHER PUBLICATIONS

Apr. 4, 2023 International Search Report issued in International Patent Application No. PCT/JP2023/002592.

(Continued)

*Primary Examiner* — Nadia A Mahmood
(74) *Attorney, Agent, or Firm* — Oliff PLC

(57) ABSTRACT

An electric potential therapy device includes a negative voltage applying means, an electrostatic charge removing means, and a controller that controls the negative voltage applying means and the electrostatic charge removing means in a predetermined therapy time in which a therapy cycle is repeated a plurality of times, the therapy cycle consisting of a first and second period. The negative voltage applying means includes a negative voltage generator and an application electrode. The negative voltage generated by the negative voltage generator is applied to the living body through the application electrode. The controller charges the living body to a negative potential in the first period by controlling the negative voltage applying means to apply the negative voltage to the living body, and puts the living body into a non-charged state by controlling the electrostatic charge removing means to remove electrostatic charges from inside the living body in the second period.

10 Claims, 21 Drawing Sheets

(58) Field of Classification Search
USPC ........................................................... 607/59
See application file for complete search history.

(56)                    References Cited

FOREIGN PATENT DOCUMENTS

| JP | 2004-183936 | A |   | 7/2004 |
|----|-------------|---|---|--------|
| JP | 2007-111186 | A |   | 5/2007 |
| JP | 3212573     | U |   | 9/2017 |
| JP | 2018-114097 | A |   | 7/2018 |
| JP | 2023-23360  | A |   | 2/2023 |
| JP | 2023023360  | A | * | 2/2023 |

OTHER PUBLICATIONS

Apr. 4, 2023 Written Opinion issued in International Patent Application No. PCT/JP2023/002592.

* cited by examiner

FIG.2

CONTROL GROUP   n=4  THERAPY GROUP n=5
ERROR BARS INDICATE
 STANDARD DEVIATION
*p<0.05 vs. CONTROL GROUP

CONTROL GROUP

THERAPY GROUP

EACH GROUP n=5
ERROR BARS INDICATE
 STANDARD DEVIATION
** p<0.01 vs. CONTROL GROUP

CONTROL GROUP                THERAPY GROUP

EACH GROUP n=6
ERROR BARS INDICATE
 STANDARD DEVIATION
** p<0.01 vs. CONTROL GROUP

EACH GROUP  n=5(4th WEEK IN CONTROL GROUP  n=4)
ERROR BARS INDICATE STANDARD DEVIATION

ELECTRIC POTENTIAL THERAPY DEVICE

TECHNICAL FIELD

The invention relates to an electric potential therapy device.

BACKGROUND OF THE INVENTION

There have been proposed electric potential therapy devices, which apply high electric potential to a human body for relieving such symptoms as stiff shoulders, headache, insomnia, chronic constipation and the like. Some electric potential therapy devices alternately apply high positive potential and high negative potential to a human body. Another electric potential therapy devices apply only high positive potential, and different electric potential therapy devices apply only high negative potential (see Patent Documents 1 and 2, for example).

RELATED ART

Patent Documents

Patent Document 1: Japanese Patent Application Publication No. HEI-10-272191
Patent Document 2: Japanese Utility Model No. 3212573

SUMMARY OF THE INVENTION

Problems to be Solved by the Invention

It is an object of the invention to provide an electric potential therapy device capable of providing cells of living bodies with charging stimulus so as to activate them by removing electrostatic charges from the living bodies after charging the living bodies with a negative charge.

An electric potential therapy device according to one aspect of invention includes: a negative voltage applying means configured to apply a negative voltage to a living body; an electrostatic charge removing means configured to remove electrostatic charges from inside the living body; and a controller configured to control the negative voltage applying means and the electrostatic charge removing means in a predetermined therapy time in which a therapy cycle is repeated a plurality of times, the therapy cycle consisting of a first period and a second period, wherein: the negative voltage applying means includes a negative voltage generator that generates a negative voltage and a first electrode connected to the negative voltage generator; the negative voltage generated by the negative voltage generator is applied to the living body through the first electrode; the controller charges the living body to a negative potential in the first period by controlling the negative voltage applying means to apply the negative voltage to the living body; and the controller puts the living body into a non-charged state by controlling the electrostatic charge removing means to remove electrostatic charges from inside the living body in the second period.

Advantageous Effects of the Invention

According to the electric potential therapy device of the one aspect of the invention,
the controller controls the negative voltage applying means and the electrostatic charge removing means so as to charge the living body to a negative potential in the first period of each therapy cycle and puts the same into a non-charged state in the second period. Because such therapy cycle is repeated multiple times, it is possible to provide cells of the living body with charging stimulus to activate them.

BRIEF EXPLANATION OF DRAWINGS

FIG. 2 is a plan view of an example of an electroconductive member with electrodes of the electric potential therapy device shown in FIG. 1.

EMBODIMENTS

First Embodiment

Figure 1:
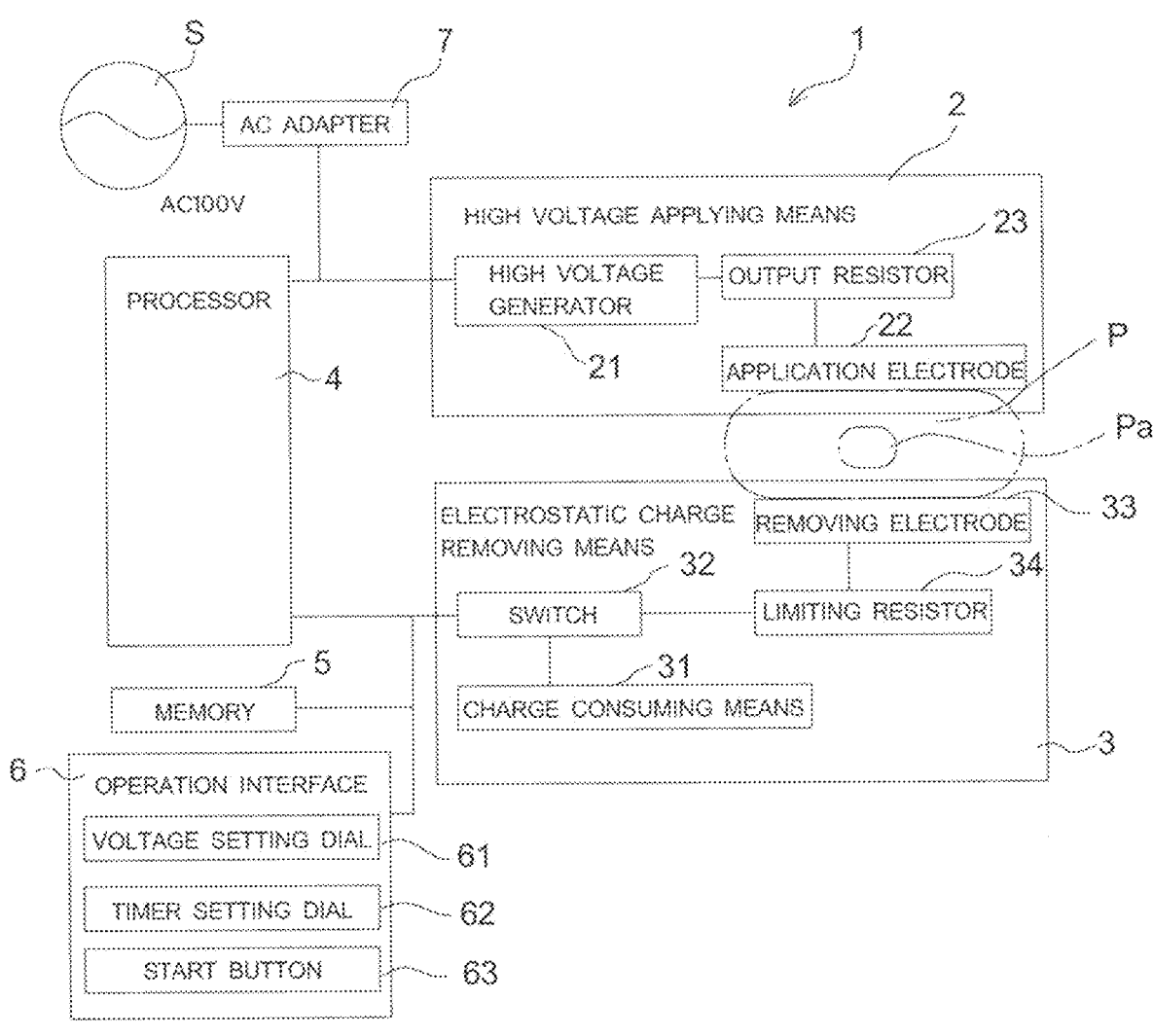
FIG. 1 is a functional block diagram of an electric potential therapy device according to a first embodiment of the invention.

An electric potential therapy device according to a first embodiment of the invention will be described with reference to attached drawings. With reference to FIG. 1, an electric potential therapy device 1 of this embodiment includes a negative voltage applying means (negative voltage applying unit) 2 for applying a negative voltage to a living body P, an electrostatic charge removing means (electrostatic charge removing unit) 3 for removing electrostatic charges from inside the living body P, a processor 4 for controlling the negative voltage applying means 2 and the electrostatic charge removing means 3, a memory 5, an operation interface 6, and an AC adapter 7. The living body P is a human body or an animal body.

The negative voltage applying means 2 includes a negative voltage generator 21 that generates a negative voltage, an application electrode 22 (first electrode) connected to the negative voltage generator 21, and an output resistor 23 interposed between the negative voltage generator 21 and the application electrode 22. The negative voltage generated by the negative voltage generator 21 is applied to the living body P via the application electrode 22. The output resistor 23 prevents an electric current from flowing from the negative voltage generator 21 to the application electrode 22. As a result, the negative voltage generated by the negative voltage generator 21 is applied to the living body P, but an electric current does not flow to the living body P.

The electrostatic charge removing means 3 includes a charge consuming means (electrostatic charge consuming member) 31, a switch 32 connected to the charge consuming means 31, a removing electrode 33 (second electrode) connected to the switch 32, and a limiting resistor 34 interposed between the switch 32 and the removing electrode 33.

The charge consuming means 31 is a power consumption resistor, for example. When the switch 32 is turned ON, then the charge consuming means 31 and the removing electrode 33 are electrically connected to each other, and electrostatic charges are removed from inside the living body P to the charge consuming means 31 and consumed by the charge consuming means 31. On the other hand, when the switch 32 is turned OFF, then the charge consuming means 31 and the removing electrode 33 are electrically disconnected from each other, and no electrostatic charge is removed from the living body P through the removing electrode 33. The switch 32 is preferably a relay switch.

The processor 4 is an arithmetic processing unit such as a CPU (Central Processing Unit) or MPU (Multi Processing Unit) and configured to function as a controlling unit (controller) to control each unit of the electric potential therapy device 1 by reading out and executing programs stored in the memory 5.

The memory 5 stores programs to be executed by the processor 4, data to be used by the processor 4, and the like.

The operation interface 6 receives input of an operation on the electric potential therapy device 1 and includes various dials and buttons. When these dials or buttons are operated by a user, signals resulting from the operation are input to the processor 4. In this embodiment, the dials of the operation interface 6 include a voltage setting dial 61 and a timer setting dial 62, and the buttons of the operation interface 6 include a start button 63.

The AC adapter 7 is electrically connected to the negative voltage applying means 2 and the processor 4. When the AC adapter 7 is connected to a commercial power supply S, then the AC adapter 7 convers a commercial power (commercial power of 100V, 60 Hz, for example) supplied from the commercial power supply S to a predetermined DC power and supplies the same to the negative voltage applying means 2 and the processor 4.

Figure 2:
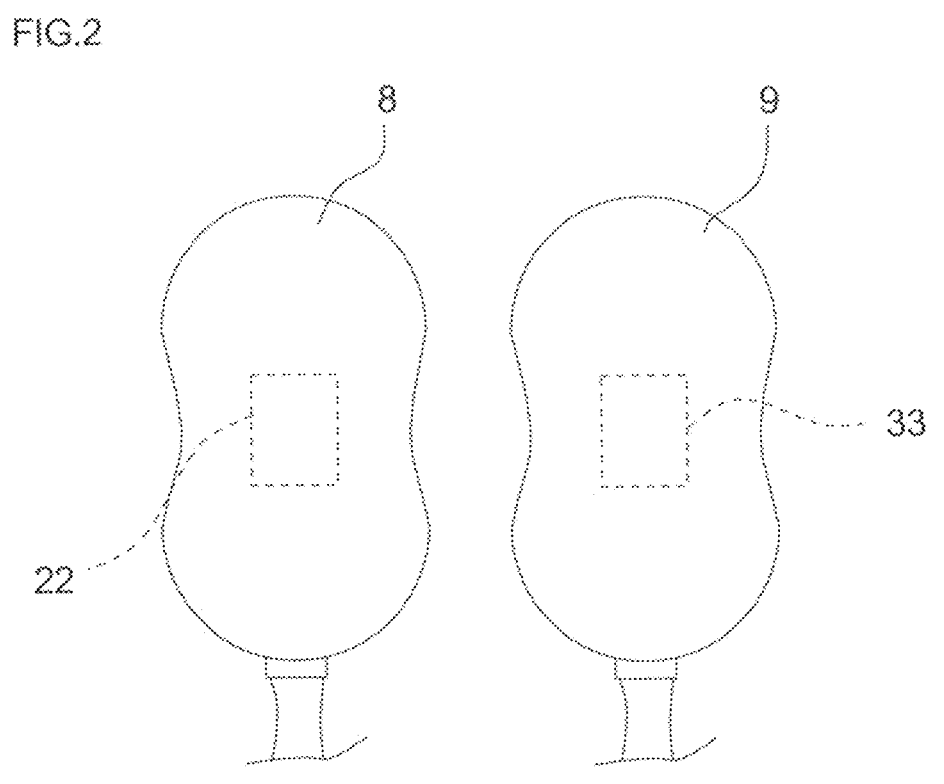

It is preferable that the application electrode 22 and the removing electrode 33 be respectively formed in such electroconductive members 8 and 9 shown in FIG. 2. In this case, when the electroconductive members 8 and 9 are mounted on the living body P, then the application electrode 22 and the removing electrode 33 are brought into electrical contact with the living body P via the electroconductive members 8 and 9. There is no limitation in the shape of the electroconductive members 8 and 9, and the electroconductive members 8 and 9 may be in the shape of a sheet, a clip, a belt, or the like. In a different embodiment, the application electrode 22 and the removing electrode 33 are formed in a single electroconductive sheet and electrically contact the living body P via the electroconductive sheet.

Figure 3:
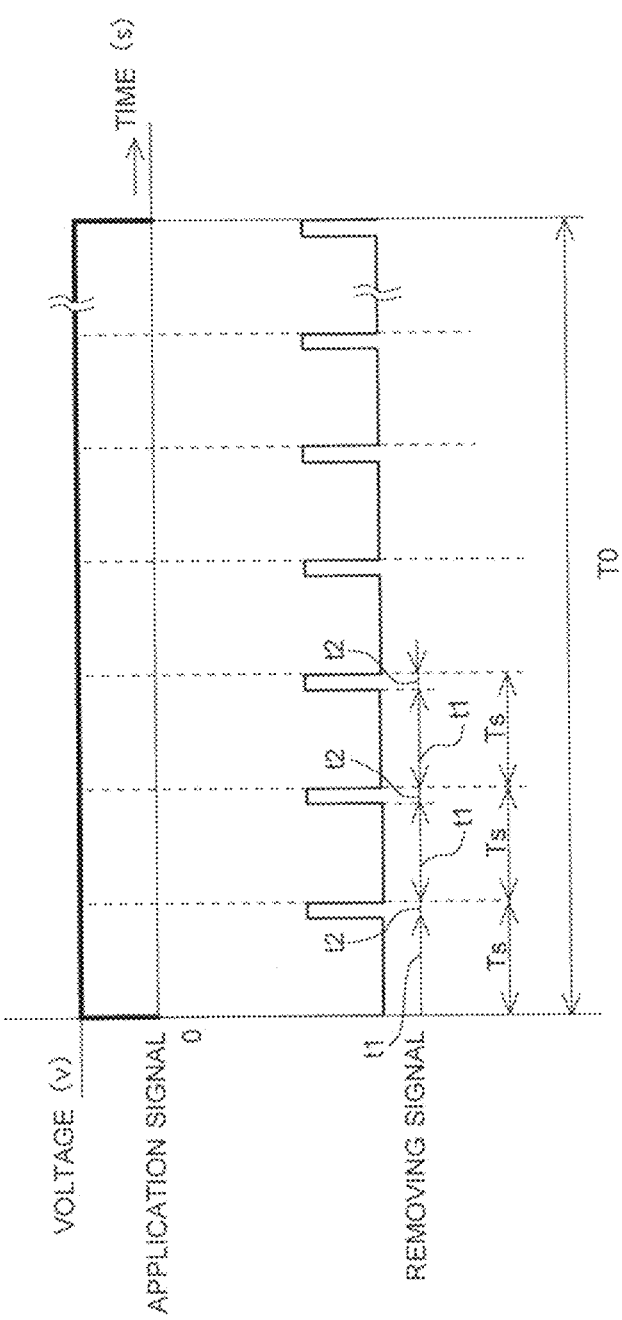
FIG. 3 is a graph showing output timings of an application signal and removing signals in the electric potential therapy device shown in FIG. 1.

With reference to FIG. 3, the electric potential therapy device 1 conducts therapy for the living body P in a therapy time T0, and a treatment cycle Ts is consecutively repeated a plurality of times in the therapy time T0. Each treatment cycle Ts includes a first period t1 and a second period t2 following the first period t1. In other words, the first period t1 and the second period t2 are consecutively repeated in the therapy time T0, and each treatment cycle Ts consists of the first period t1 and the second period t2.

The processor 4 controls the negative voltage applying means 2 and the electrostatic charge removing means 3 to charge the living body P with a negative electrostatic potential in each first period t1 and to remove electrostatic charges from the living body P in each second period t2.

More specifically, as shown in FIG. 3, the processor 4 outputs an application signal to the negative voltage applying means 2 (the negative voltage generator 21) during the entire therapy time T0 and a removing signal to the electrostatic charge removing means 3 (the switch 32) during the second periods t2. That is, the processor 4 generates and outputs the application signal but not the removing signal during the first periods t1, and generates and outputs both the application signal and the removing signal during the second periods t2.

Receiving the application signal from the processor 4, the negative voltage applying means 2 generates and applies a negative voltage to the living body P. That is, the negative voltage applying means 2 continuously applies a negative voltage of a predetermined value to the living body P in the entire therapy time T0.

Receiving the removing signal from the processor 4, the electrostatic charge removing means 3 removes electrostatic charges from the living body P. That is, the electrostatic charge removing means 3 removes electrostatic charges from the living body P in the second period t2 of each treatment cycle Ts.

In this embodiment, the switch 32 is a relay switch, and when the removing signal from the processor 4 is input to the switch 32, then the switch 32 (the relay switch) is turned ON. As a result, the removing electrode 33 is electrically connected to the charge consuming means 31, and electrostatic charges in the living body P are removed via the switch 32 to the charge consuming means 31 and consumed.

On the other hand, when the removing signal is not input to the electrostatic charge removing means 3 from the processor 4, then the switch 32 (the relay switch) is turned OFF. As a result, the removing electrode 33 is electrically disconnected from the charge consuming means 31, and no electrostatic charge in the living body P is removed through the switch 32.

Figure 4:
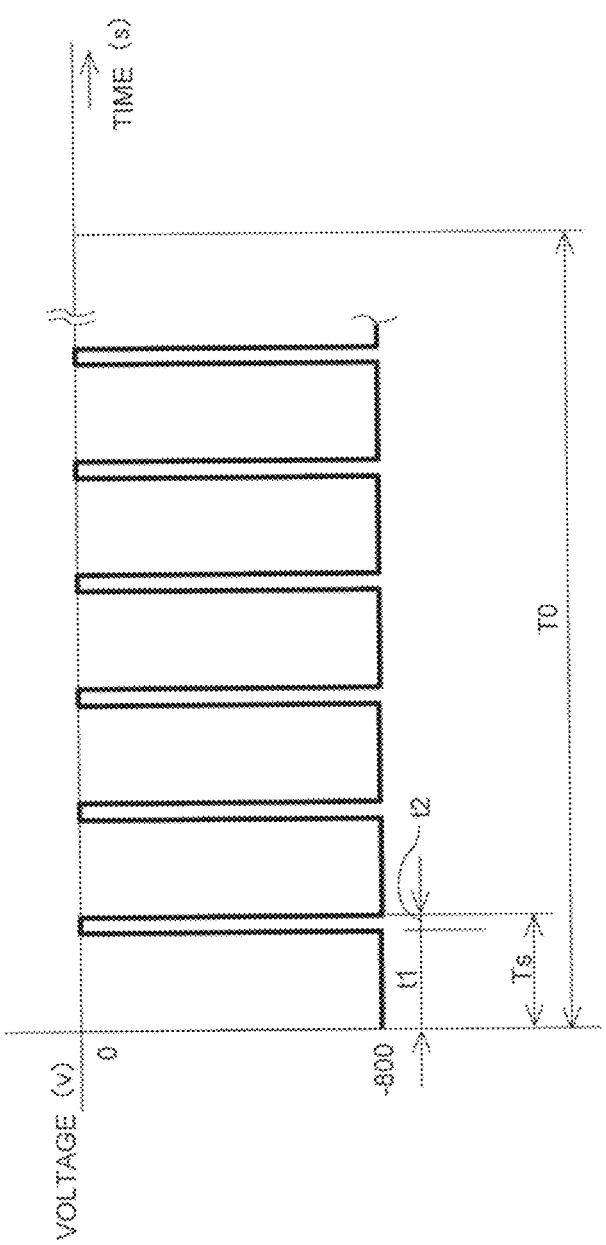
FIG. 4 is a graph showing timings at which the electric potential therapy device shown in FIG. 1 removes electrostatic charges from inside a living body.
Figure 5:
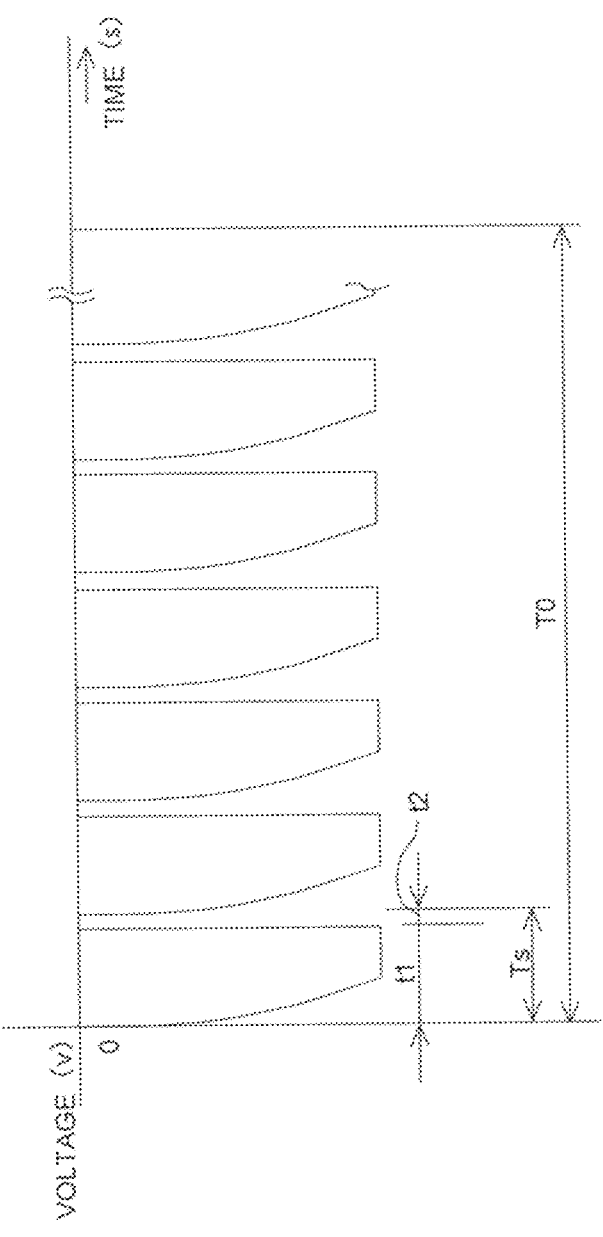
FIG. 5 is a graph showing a charging state of the living body when the electric potential therapy device shown in FIG. 1 is conducting an electric potential therapy on the living body.

Thus, the timing at which electrostatic charges are removed from inside the living body P by the electric potential therapy device 1 is as shown in FIG. 4, and the state of charge of the living body P is as shown in FIG. 5.

Thus, inside the living body P is negatively charged in the first period t1 of each treatment cycle Ts by a negative voltage applied by the negative voltage applying means 2, and electrostatic charges are removed in the second period t2 from inside the living body P by the electrostatic charge removing means 3, bringing the living body P into a non-charged state.

It should be noted that the electrostatic charges that the electrostatic charge removing means 3 removes from the living body P include a positive (+) electrostatic charge and a negative (−) electrostatic charge existing inside the living body P and a negative (−) electrostatic charge accumulated by application of a negative voltage by the negative voltage applying means 2.

The limiting resistor 34 prevents the electrostatic charges removed from the living body P by the electrostatic charge removing means 3 from returning to the living body P, and also regulates a bioelectric current that flows through an epidermis of the living body P at removal of electrostatic charges, preventing excessive stimulation of nerves.

The voltage setting dial 61 is configured of a rotary encoder, for example, and a user can rotate the voltage setting dial 61 to set a value of the voltage that the negative voltage applying means 2 applies to the living body P.

The timer setting dial 62 is configured of a rotary encoder, for example, and a user can rotate the timer setting dial 62 to set a duration of the therapy time T0 (hereinafter referred to as "therapy time duration").

In this embodiment, the voltage applied to the living body P by the negative voltage applying means 2 is a high voltage, and a value of the high voltage is preferably −600 V to −3600 V. If the voltage value is less than −600 V, then there is a danger that sufficient activating stimulus will not be provided to the living body P because a voltage difference (potential difference) between a non-charged state and a charged state is too small. If the value is greater than −3600 V, then there is a danger that reflex (autonomic reflex and the like) of the living body P will be undesirably strong.

A time duration of the first period t1 is preferably 5 seconds to 30 seconds. If the time duration of the first period t1 is less than 5 seconds, then there is a danger that the epidermis of the living body P is harmed because a bioelectric current that flows through the epidermis of the living body P at the removal of electrostatic charges occurs too frequently. On the other hand, if the time duration of the first period t1 is longer than 30 seconds, then there is a danger that sufficient activating stimulus is not provided to the living body P because an occurrence interval of the second period t2, in which the living body P is brought into the non-charged state, is too large.

A time duration of the second period t2 is preferably ¹⁄₁₀₀₀ seconds (1 ms) to ¹⁄₂₀₀ seconds (5 ms). If the time duration of the second period t2 is longer than ¹⁄₂₀₀ seconds (5 ms), then there is a danger that a bioelectric current occurring at the removal of electrostatic charges may chemically react with sodium in the epidermis, causing damage to the epidermis.

The therapy time duration is preferably 1 minute to 60 minutes. Although the therapy time duration is determined based on a symptom of the living body P, a use frequency of the electric potential therapy device 1, a build of the living body P, and the like, if the therapy time duration exceeds 60 minutes, then there is a danger that the living body P may develop a tolerance for charge stimulus, degrading effects of the therapy.

Next, a method of electric potential therapy using the electric potential therapy device 1 will be described. First, a user operates the voltage setting dial 61 to set the value of voltage (−800 V, for example) to be applied to the living body P and the timer setting dial 62 to set the therapy time duration (20 minutes, for example).

Then, the user puts the application electrode 22 and the removing electrode 33 into electrical contact with the living body P by placing the electroconductive members 8 and 9 on the living body P, for example.

After the user operates the start button 63, the processor 4 continuously outputs the application signal to the negative voltage applying means 2 in the entire therapy time T0 (for 20 minutes, for example) and outputs the removing signal to the electrostatic charge removing means 3 in the second period t2 of each treatment cycle Ts.

As a result, in the first period t1, negative electrostatic charges are accumulated in the living body P due to the negative voltage (negative high voltage) applied to the living body P, bringing the living body P into a negatively charged state. As a result, oxidized substances (which are positively charged) accumulated in the living body P due to external and/or internal factors, and oxidized visceral tissues (which are positively charged) are filled with negative charges (−).

Also, in the second period t2 following the first period t1, the switch 32 is turned ON, and electrostatic charges are removed from inside the living body P to the charge consuming means 31. This forces the living body P into a non-charged state (±0 charge).

Repetition of such first period t1 and second period t2 alternately brings the living body P into the negatively charged state and the non-charged state without bringing the living body P into a positively charged state. This induces oxidized blood, fluid, and viscera from a positive (+) charge to a negative (−) charge, gradually restoring a charge balance of the living body P and reducing oxidative stress.

That is, in the living body P that produces energy using oxygen, reactive oxygen species (ROS) are produced in metabolism process. While ROS is vital, it is known to oxidize and harm cells of the living body P. The living body P possesses an antioxidant function for preventing adverse effects of oxidation by ROS, and health of the living body is maintained by homeostasis. A state where oxidation is excessive due to imbalance between oxidation and antioxidation is called an oxidative stress.

Also, both positive charges and negative charges always exist in the living body P. When oxidation progresses in cells, the living body P ends up in a positively charged state with more positive charge, and a charge balance is disrupted. When the charge balance is resumed in the living body P, on the other hand, then oxidative stress and various oxidative stress disorders are relieved.

The electric potential therapy device 1 of this embodiment resumes the charge balance in the living body P by repeatedly bringing the living body P into the negatively charged state and the non-charged state alternately without bringing the living body P into the positively charged state as described above.

Second Embodiment

Figure 6:
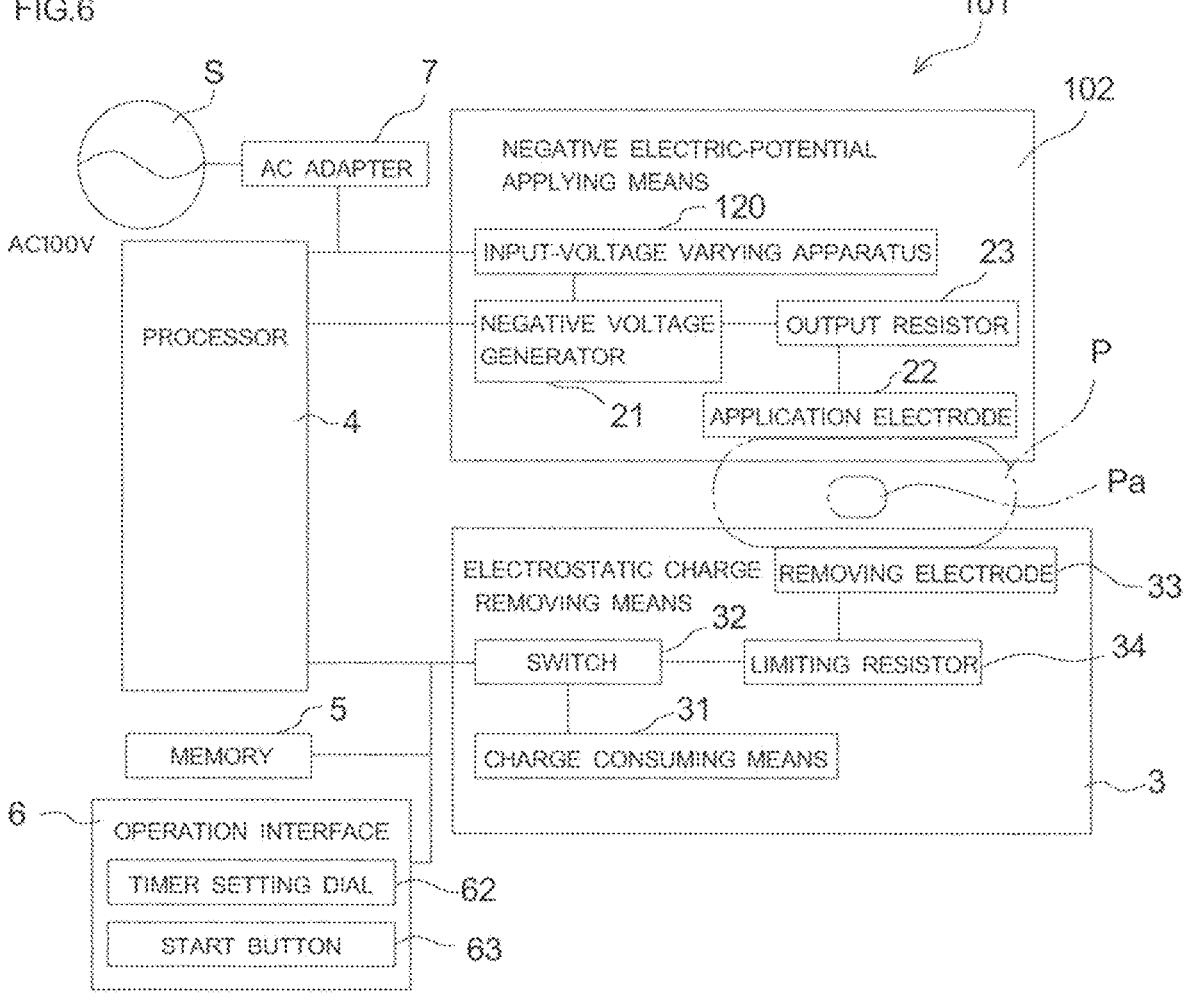
FIG. 6 is a functional block diagram of an electric potential therapy device according to a second embodiment of the invention.

Next, an electric potential therapy device according to a second embodiment of the invention will be described. With reference to FIG. 6, an electric potential therapy device 101 of this embodiment is substantially the same as the above-described electric potential therapy device 1, but includes a negative voltage applying means (negative voltage applying unit) 102 instead of the negative voltage applying means 2, and the negative voltage applying means 102 includes an input-voltage varying apparatus 120 in addition to the negative voltage generator 21, the application electrode 22, and the output resistor 23 described above. Also, the voltage setting dial (61) is dispensed with.

The input-voltage varying apparatus 120 is electrically connected to the AC adapter 7, varies a voltage of the DC power supplied from the AC adapter 7, and outputs the same to the negative voltage generator 21. The processor 4 outputs the above-described application signal and the removing signal to the negative voltage generator 21 and the switch 32, respectively, and also inputs a voltage control signal to the input-voltage varying apparatus 120. The input-voltage varying apparatus 120 varies the value of the voltage to be output to the negative voltage generator 21 in accordance with the voltage control signal from the processor 4.

It should be noted that the processor 4 controls the input-voltage varying apparatus 120 via the voltage control signal such that the value of the negative voltage output from the input-voltage varying apparatus 120 to the negative voltage generator 21 varies either at random or in a predetermined pattern.

As a result, the value of negative voltage generated by the negative voltage generator 21 and output to the living body P varies within a predetermined range. Although this range may be arbitrarily set, the range is preferably –600 V to –3600V.

Figure 7:
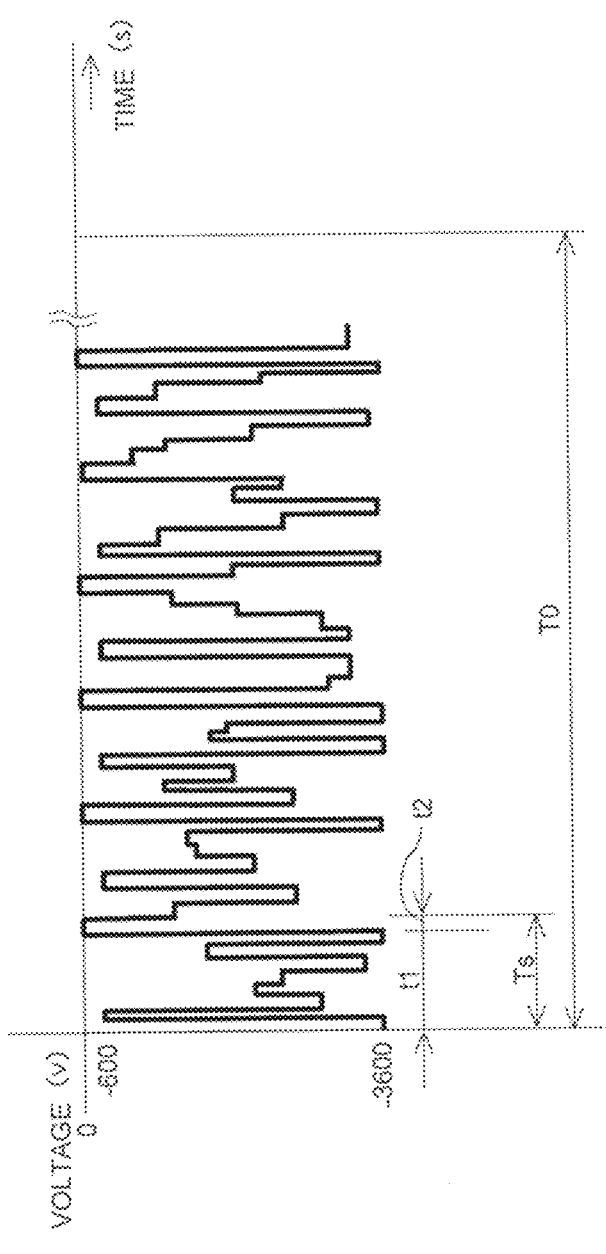
FIG. 7 is a diagram explaining change in a value of electric potential that the electric potential therapy device shown in FIG. 6 applies to the living body.

Thus, the value of the electric potential applied to the living body P in the first period t1 of each treatment cycle Ts varies as shown in FIG. 7.

In comparison with the first embodiment where a constant voltage is applied to the living body P, varying the value of the voltage to be applied to the living body P either at random or in a predetermined pattern as described above inhibits development of tolerance against activating stimulus to tissues and the like of the living body P, thereby enhancing the effects of the activating stimulation of the living body P and leading to shortening of the therapy time.

It should be noted that the processor 4 generates the voltage control signal by executing a predetermined control program stored in the memory 5, for example.

First Modification

Figure 8:
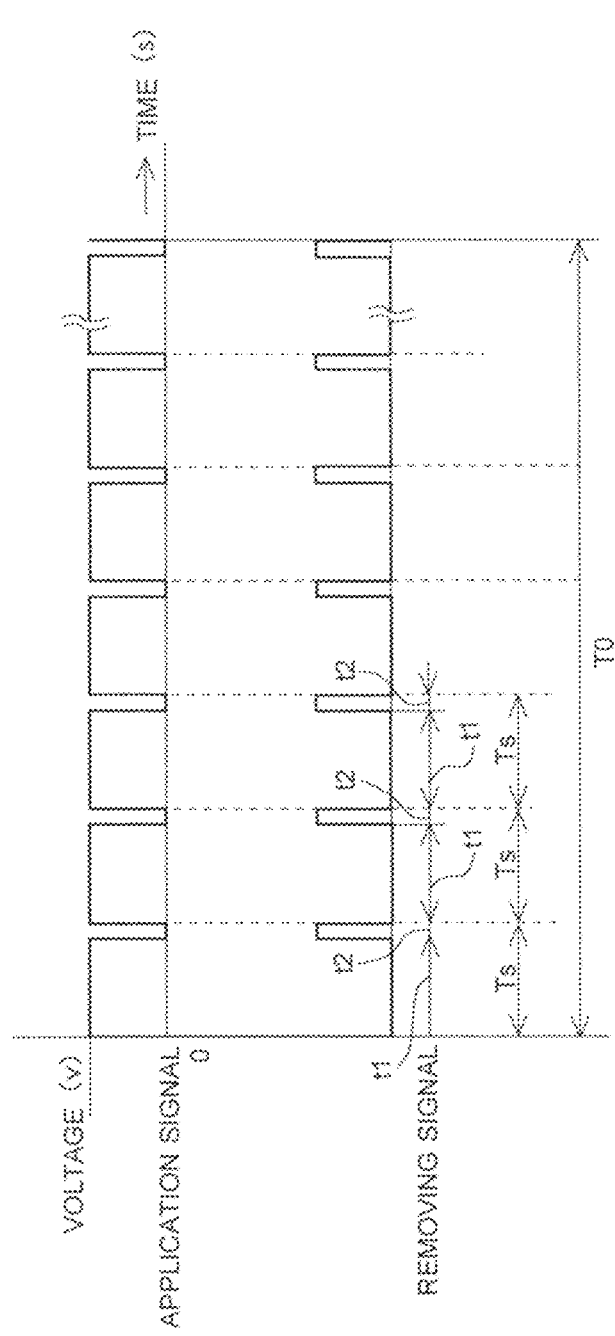
FIG. 8 is a graph showing output timings of application signals and removing signals in an electric potential therapy device according to a first modification of the embodiments of the invention.

Next, an electric potential therapy device according to a first modification of the first and second embodiments will be described. Although the processor 4 outputs the application signal in the entire therapy time T0 in the above embodiments, as shown in FIG. 8, the processor 4 in this modification outputs the application signal in the first period t1 of each treatment cycle Ts but not in the second period t2. In this modification also, the living body P is negatively charged in the first period t1 and brought into the non-charged state in the second period t2 because electrostatic charges are removed from the living body P in the same manner as described above.

Second Modification

Figure 9:
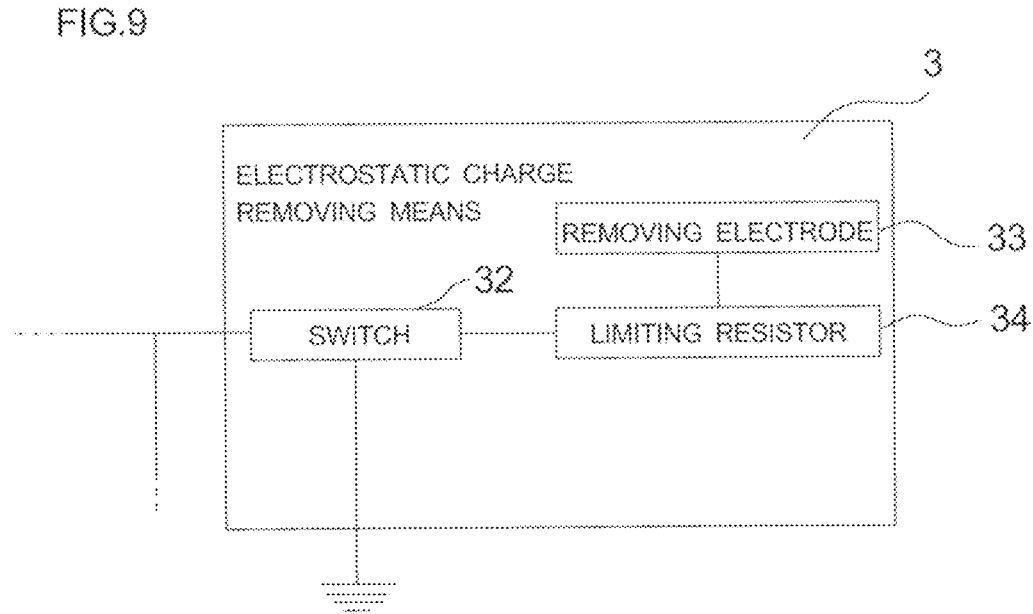
FIG. 9 is a functional diagram of a negative voltage applying means that an electric potential therapy device according to a second modification of the embodiments of the invention includes.

Next, an electric potential therapy device according to a second modification of the first and second embodiments will be described. Although the electrostatic charge removing means 3 consumes electrostatic charges removed from the living body P with the charge consuming means 31 in the above embodiments, in this modification, as shown in FIG. 9, the electrostatic charge removing means 3 does not include the charge consuming means 31, and the switch 32 is connected to the earth ground. Thus, when the switch 32 is turned ON, then the removing electrode 33 is electrically connected to the earth ground, and electrostatic charges removed from the living body P are discharged to the earth ground through the switch 32.

Third Modification

Next, a third modification of the first and second embodiments will be described. Although the electric potential therapy device 1 includes one application electrode 22 and one removing electrode 33 in the above embodiments, the electric potential therapy device of this modification includes two or more (four, for example) application electrodes 22. In this case, these application electrodes 22 are put on the living body P such that two of them electrically contact either arm and that the other two either ankles, for example. In a different modification, an electric potential therapy device includes two or more removing electrodes 33.

First Example

An experiment was conducted to explore the effects of the above-described electric potential therapy device 1. This experiment was performed on db/db mice, mouse models of type 2 diabetes mellitus.

(1) General Description of Experiment 10 male mice (db/db mice) of 7 weeks old were purchased, preliminarily raised for three days, and used for testing. These mice were divided at random into a therapy group of five and a control group of five, and an electric potential therapy was conducted on only those in the therapy group using the electric potential therapy device 1.

A therapy period was 28 days (4 weeks). The electric potential therapy was performed on the db/db mice in the therapy group twice daily in the morning and afternoon with an eight-hour interval. The value of application voltage was –1000 V, and the therapy time duration was 30 minutes.

Figure 10:
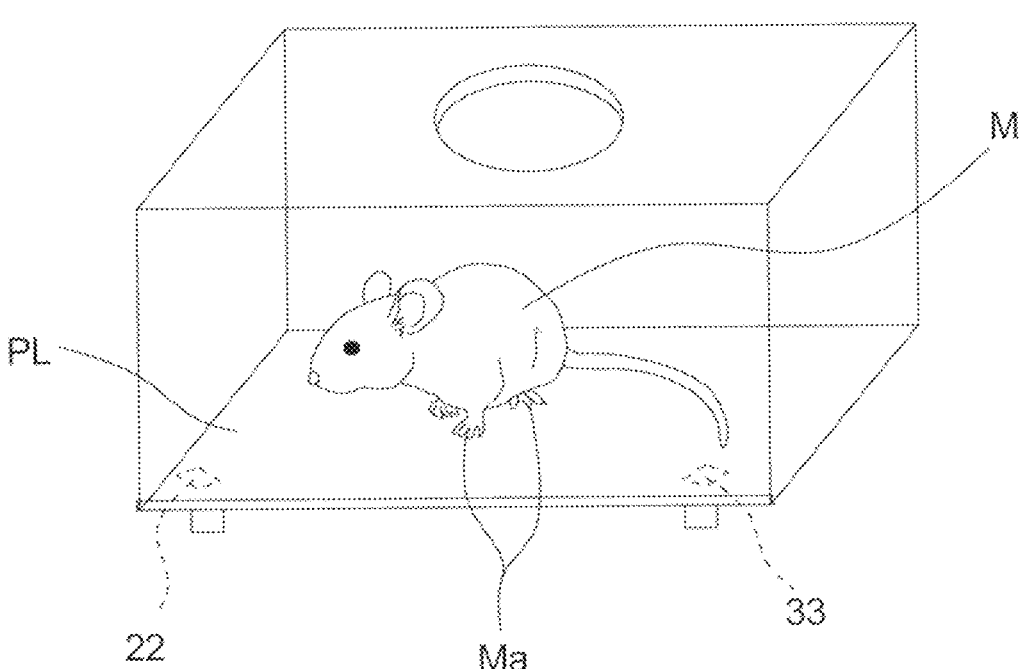
FIG. 10 is a view explaining a method to conduct an electric potential therapy on mice in a first example.

As shown in FIG. 10, the electric potential therapy was performed by placing mice M in the therapy group on an electrically conductive metal plate PL connected with the application electrode 22 and the removing electrode 33. That is, the mice M contacted the metal plate PL with hairless pads Ma and thus electrically contacted the application electrode 22 and the removing electrode 33 via the metal plate PL. The electric potential therapy was performed on the mice M by repeatedly and alternately bringing the metal plate PL into a "negatively charged (–)" state and a "non-charged (±0 charge)" state.

(2) Collecting Urine Samples

Urine was collected for 24 hours using a urine cage before the therapy (hereinafter referred to as "0th week") and in the 4th week of the therapy, and urine samples were collected.

(3) Measuring Weights

Weights were measured in the 0th week and after the therapy on the last day.

(4) Collecting Plasma Samples

About 150 μL blood was collected as a 0th-week blood sample through a tail vein. Also, entire blood was collected as a 4th-week blood sample under anesthesia after the therapy on the last day. Considering effects on analytical kits to be used, only heparin sodium was used as anticaking agent. Thus collected blood samples were centrifuged at a centrifugal acceleration of 1000×g for 15 minutes to collect supernatant (plasma samples).

(5) Collecting Kidney Samples

After collecting the entire blood as described in the above (4), they were perfused with phosphate buffered saline (PBS) and underwent complete blood removal, and then left kidneys were extracted (first kidney samples).

Also, right kidneys were perfused with fixative to fix their tissues and then extracted. Some of the right kidneys were immersed in 10% formalin, paraffin-embedded, and then sliced into 4 μm thickness with a microtome to obtain kidney paraffin sections.

Further, the other right kidneys were immersed in 10% formalin for 16 hours and then sliced extremely thin (100 nm) to obtain second kidney samples.

(6) Analyzing Urine Samples

Albumin in the urine samples collected as described above was detected. Specifically, albumin in the urine samples was separated by electrophoresis using 10% poly-acrylamide (SDS-PAGE) and dyed with Coomassie Brilliant Blue (CBB). Then, the gel was scanned with a scanner. Scanned data was input to a computer and compared with albumin standard using the image analysis software ImageJ, and the amount of albumin was determined. The results are shown in FIG. 11.

Figure 11:
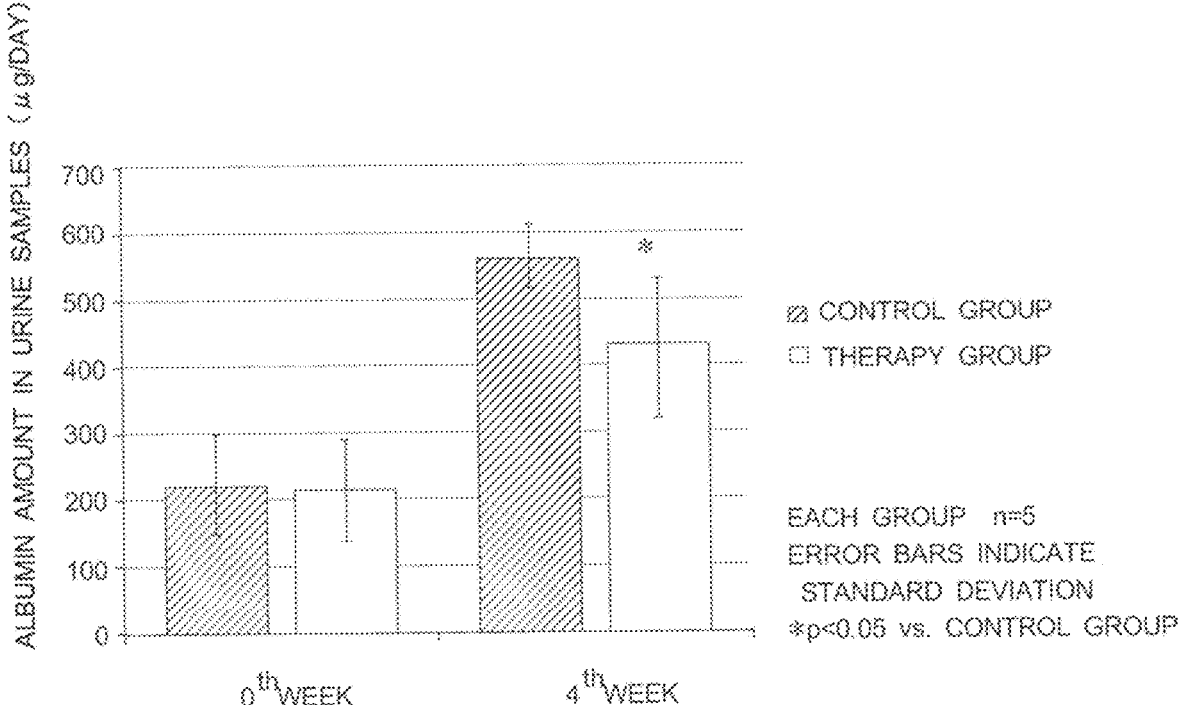
FIG. 11 is a graph showing albumin amounts in urine samples in the first example.

As shown in FIG. 11, although the amount of albumin in the urine samples significantly increased in either group from the 0th week to the 4th week, resulting from progress in diabetes, increase in the amount of albumin in the urine was significantly lower in the therapy group than in the control group.

(7) Measurement Results of Oxidative Stress in Whole Bodies

In order to measure oxidative stress in whole bodies, dROMs (one of oxidative stress markers) in the plasma samples was measured using a redox analyzer "REDOKLI-BRA 2" (manufactured by WISMERLL Co., Ltd.). The analyzer was used according to its manual. The results are shown in FIG. 12.

Figure 12:
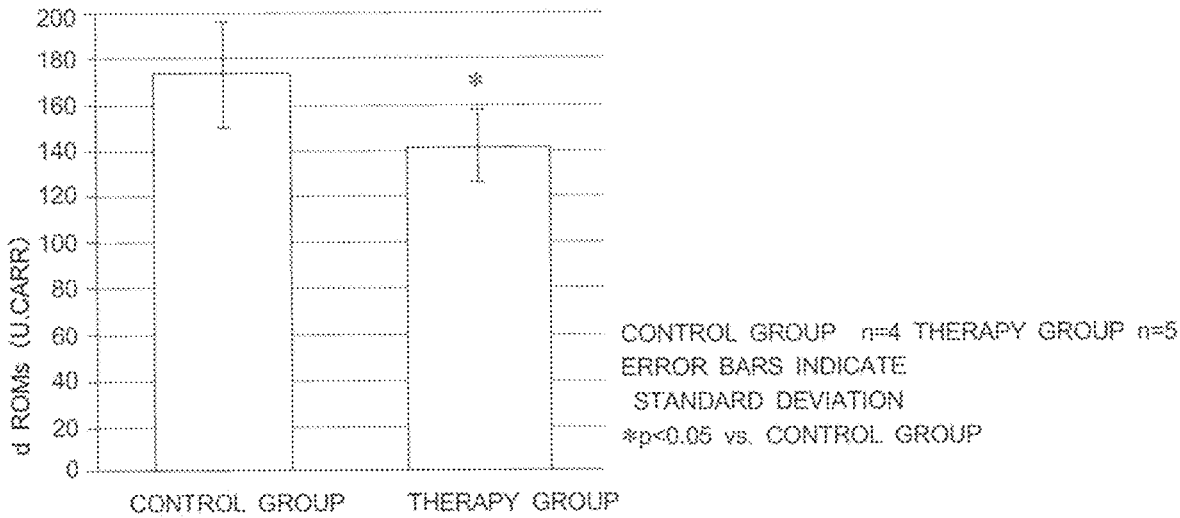
FIG. 12 is a graph showing dROMs (U.CARR) values in the first example.

As will be understood from FIG. 12, the value of dROMs after the therapy was significantly lower in the therapy group than in the control group. This indicates the possibility that oxidative stress in blood, which is increased by diabetes, had decreased in the therapy group.

(8) Detecting Oxidative Stress in Kidneys

In order to detect oxidative stress in kidneys, acrolein in the tissues in the above-mentioned first kidney samples was observed. Specifically, the left kidneys were cut into halves in a sagittal plane and further into three in a transaxial plane to obtain kidney pieces. The kidney pieces were stained by being immersed in a 20 μmol/L acrolein-RED (staining reagent produced by Funakoshi Co., Ltd.) (1:100) for 30 minutes. Then, the kidney pieces were washed with PBS four times and formed into frozen blocks. The frozen blocks were sliced into 8 μm thickness, fixed, stained with DAPI, enclosed with cover glass, and observed under a confocal microscope.

Figure 13:
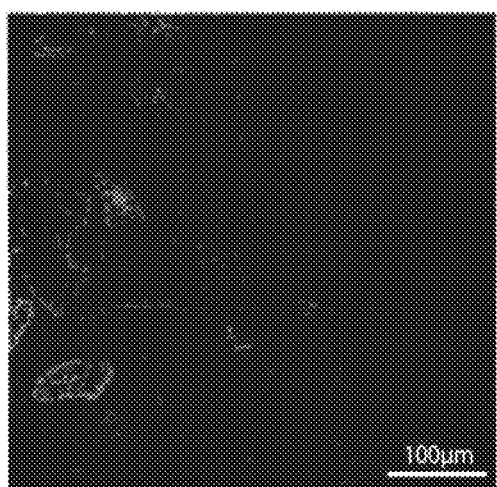
FIG. 13 shows micrographs of acrolein-RED staining results in the first example.
Figure 13:
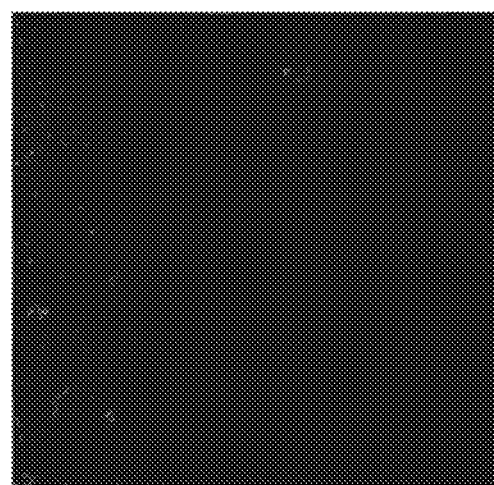
Figure 14:
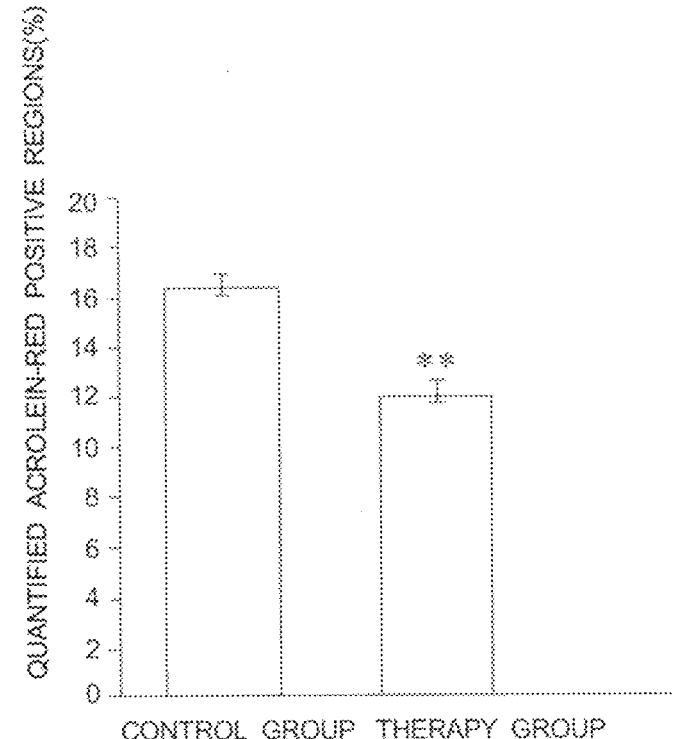
FIG. 14 shows graphs of quantified acrolein-RED positive regions in FIG. 13.

FIG. 13 shows micrographs of acrolein-RED staining results, and FIG. 14 shows graphs of quantified acrolein-RED positive regions. The amount of acrolein in the kidneys had increased in the control group but significantly decreased in the therapy group compared with the control group.

(9) Staining Desmin

The above-mentioned kidney paraffin sections were boiled in citrate buffer for 15 minutes for antigen retrieval, permeabilized with 0.1% Triton X-100 (Union Carbide Corporation) as permeabilizing reagent, and blocked with 3% skim milk. Primary antibodies were diluted in blocking solution, incubated overnight at 4° C., and incubated at room temperature for one hour together with fluorochrome-labeled secondary antibodies.

Antibodies used were as follows.
Anti-nephrin guinea pig polyclonal (Cat. No. GP-N2)—1:300 (Progen)
Anti-desmin rabbit monoclonal (Clone D93F5, Cat. No. 5332)—1:300 (Cell Signaling Technology)
Alexa Fluor 488 or 555 goat anti-rabbit—1:1000 (Thermo Fisher Scientific)
Alexa Fluor 488 or 555 goat anti-mouse—1:1000 (Thermo Fisher Scientific)

Figure 15:
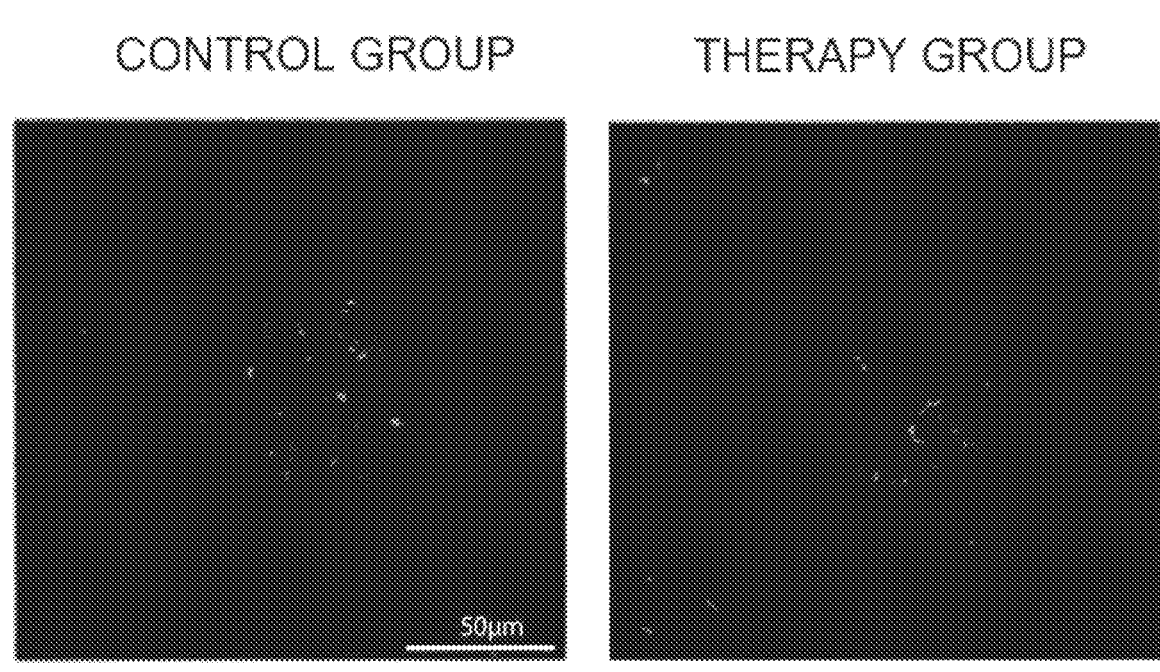
FIG. 15 shows micrographs of desmin staining results in the first example.
Figure 16:
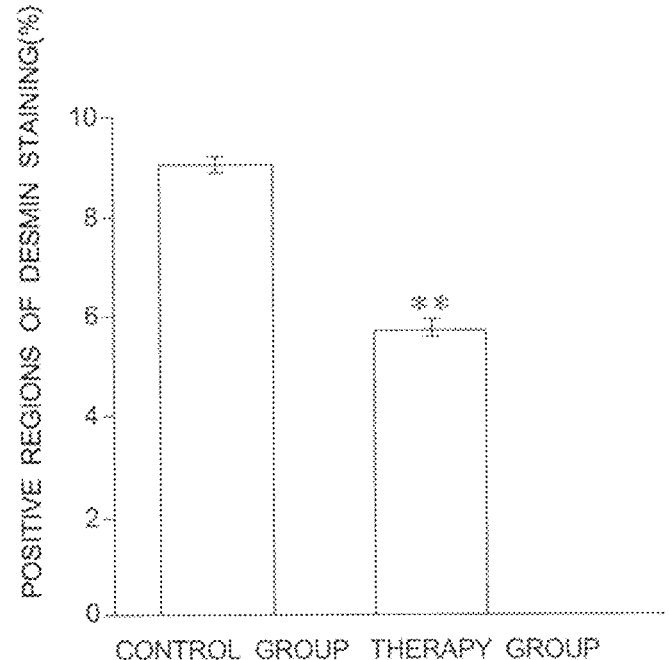
FIG. 16 shows graphs of quantified positive regions of FIG. 15.

FIG. 15 shows micrographs of desmin staining results. FIG. 16 shows graphs of quantified positive regions of desmin staining. While the desmin accumulation amount in the renal glomeruli was high in the control group, the desmin accumulation amount in renal glomeruli was significantly suppressed in the therapy group compared with that in the control group.

(10) Electron Microscope Analysis of Ultrastructural Changes in Renal Glomeruli Ultrastructures of podocyte foot processes in the glomeruli of the above-mentioned second kidney samples were observed under a scanning electron microscope and a transmission electron microscope.

Figures 17A, 17B:
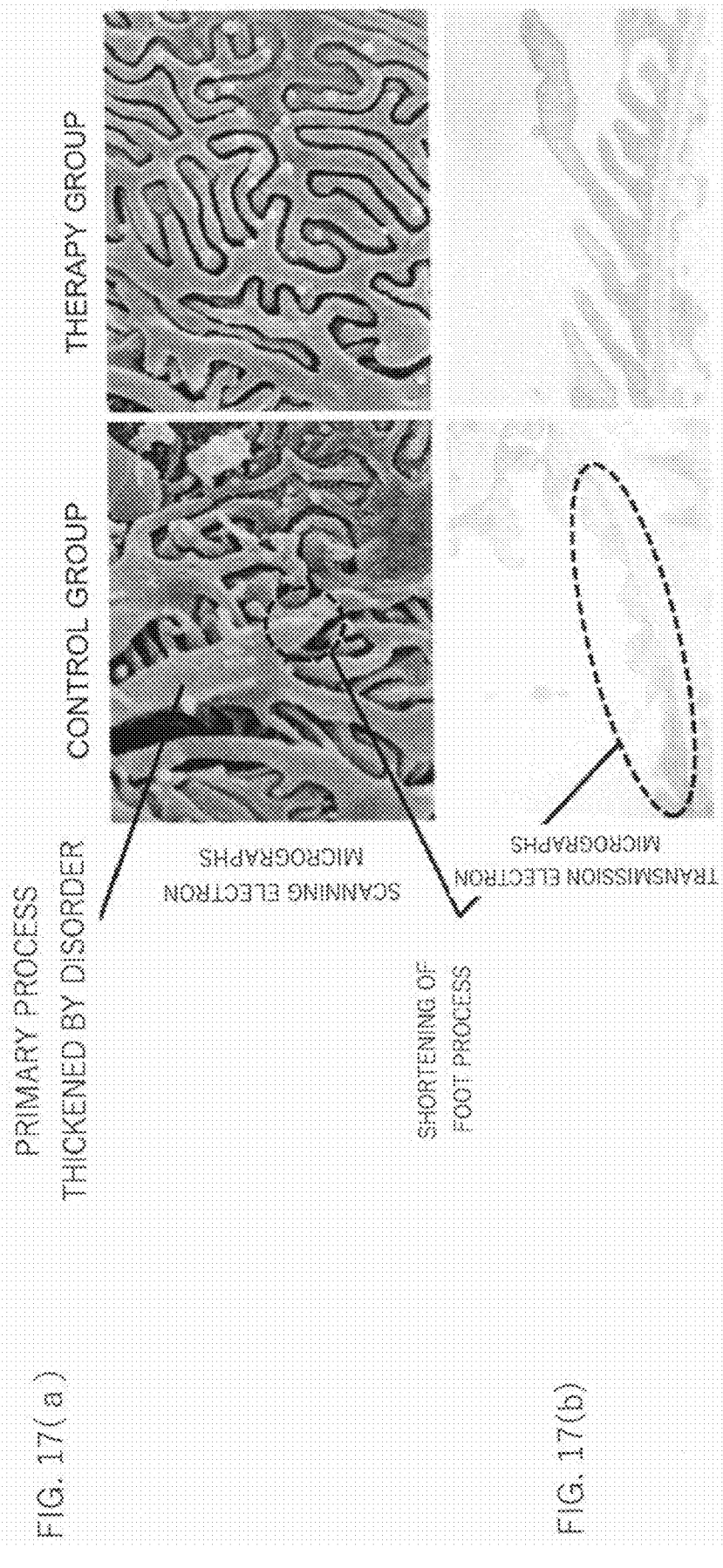
FIG. 17(a) shows scanning electron micrographs of ultra-structures of podocyte foot processes in glomeruli of the first example.
FIG. 17(b) shows transmission electron micrographs thereof.

FIG. 17(a) shows scanning electron micrographs. In the control group, primary processes of the podocytes had thickened and shortened. Shortening of foot processes impaired the orderly arrangement of the foot processes, causing gaps therebetween. Shortening (or disappearance) of such foot processes results in leakage of protein through the gaps between the foot processes, results in proteinuria. In the therapy group, such manifestations have reduced.

Also, FIG. 17(*b*) shows transmission electron micrographs. Here, the observation focused more on foot processes branching from primary processes. In the control group, the foot processes had shortened, and podocyte damages were observed. Podocytes in the therapy group remained longer in length than those in the control group.

(11) Analyzing Body Weights and Plasma Samples

Figure 18:
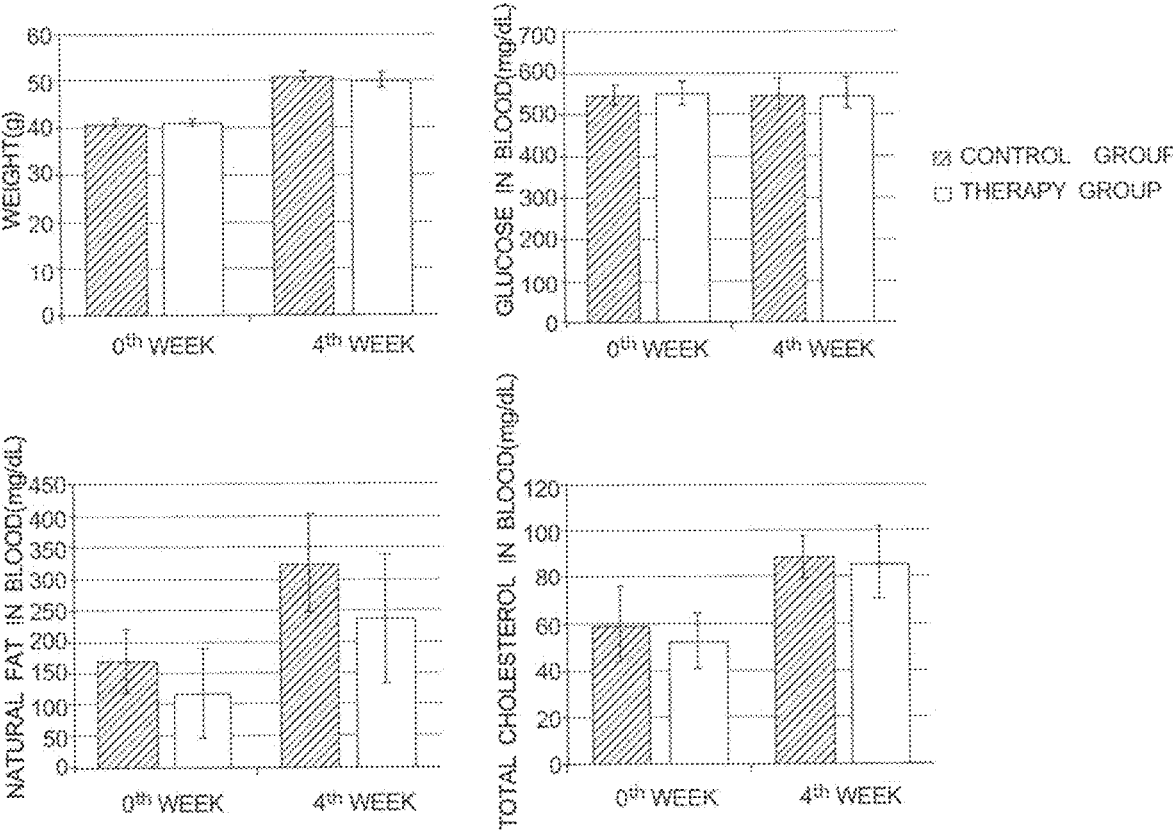
FIG. 18 is a graph showing analysis results of body weights and plasma samples in the first example.

Concentrations of glucose, natural fat, and total cholesterol in blood were measured. As will be understood from FIG. 18, the weights and all of the concentration measurement values had increased over time, but there was no significant difference between the two groups.

From the above, it is determined that the electric potential therapy using the electric potential therapy device 1 is effective in suppressing urine albumin excretion, relieving blood oxidative stress indicated by dROMs and renal oxidative stress indicated by the acrolein amount, and reducing the desmin accumulation amount indicating damages in renal glomeruli.

Because the concentrations of glucose, natural fat, and total cholesterol in blood were not affected, it is indicated that relieving effects on kidney failure resulting from progress in diabetes were resulted from reduction of oxidative stress (dROMs, acrolein, and the like), and it is believed that the electric potential therapy using the electric potential therapy device 1 of this embodiment effectively reduced oxidative stress in blood and kidneys, resulting in significant reduction of the amount of albumin in urine (that is, kidney failure was suppressed).

While ROS, especially hydroxyl radical, used to be thought of as the main cause of oxidative stress, recent studies have found that acrolein enhances oxidative stress disorders. Acrolein is strong oxidant tens of times more toxic than hydroxyl radical, and decrease of acrolein leads to relieving of oxidative stress disorders. Thus, it is believed that effects of decreasing acrolein through the electric potential therapy using the electric potential therapy device 1 of this embodiment are profound.

Thus, the electric potential therapy device 1, 101 according to the above embodiments and their modifications can be used as a kidney disease therapy device, an oxidative stress reducing device, an acrolein reducing device, and the like.

Figure 19:
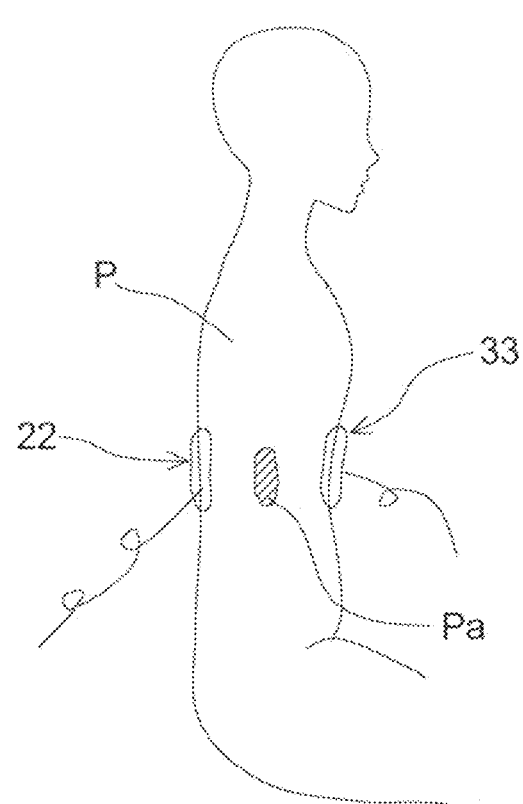
FIG. 19 is a diagram showing an example of how to put the application electrode and the removing electrode on the living body.

When the electric potential therapy device 1 (101) is used as the kidney disease therapy device, it is preferable that as shown in FIGS. 1 and 19 the application electrode 22 be put on a back of the living body P and the removing electrode 33 on a belly such that a kidney Pa is located between the application electrode 22 and the removing electrode 33.

Second Example

Figure 20:
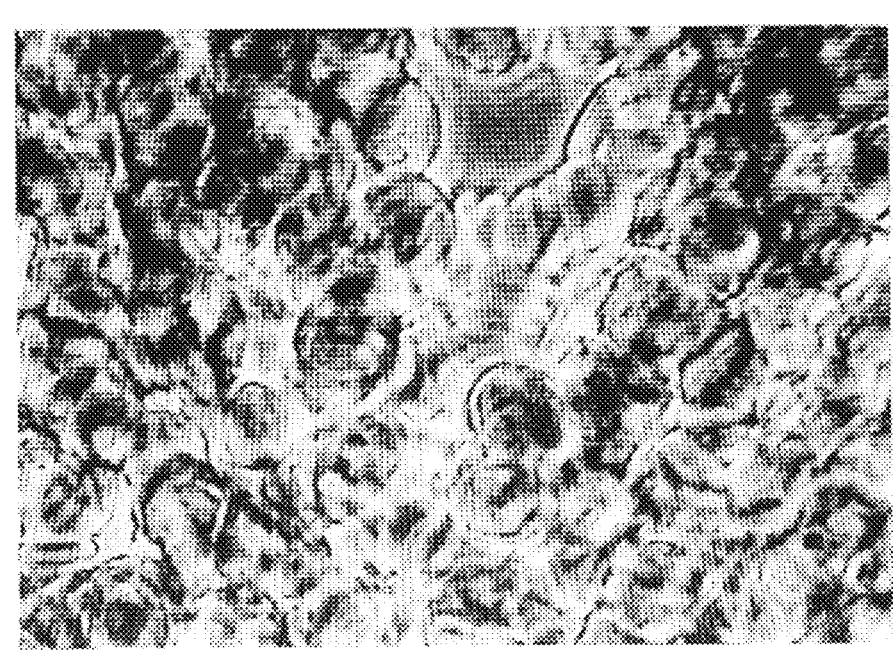
FIG. 20(a) is a phase contrast microscope photograph showing blood before an electric potential therapy device was used in a second example.
FIG. 20(b) is a phase contrast microscope photograph showing blood after the electric potential therapy device was used in the second example.
Figure 20:
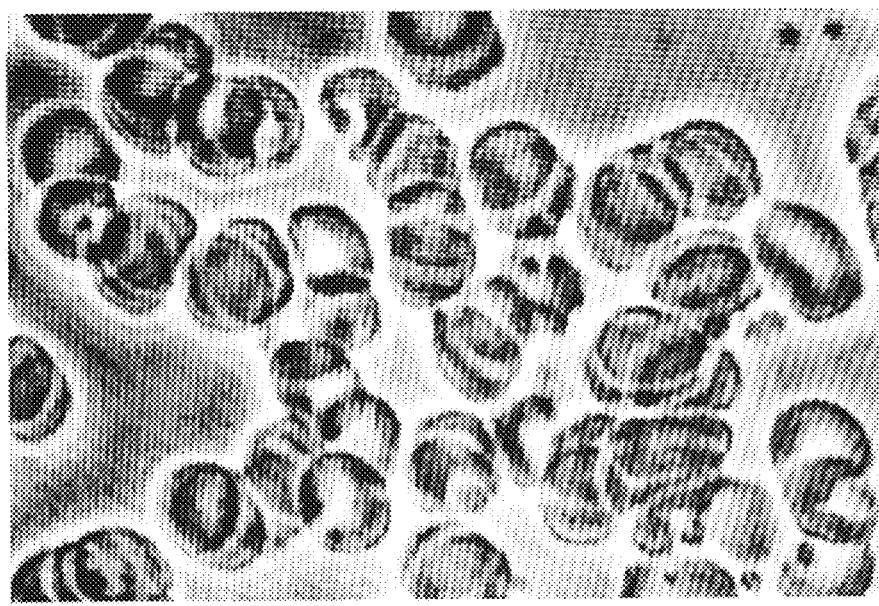

Blood was collected from a man in his 50's and observed under a phase contrast microscope. FIG. 20(*a*) shows a condition of the blood before the electric potential therapy device 1 was used on the man, and "aggregated red blood cells," which are unmoving red blood cells clumped together, were observed. FIG. 20(*b*) shows a condition of the blood after the electric potential therapy device 1 was used on the man (the electric potential therapy device 1 was used once; the applied voltage was −1000 V, the time duration of use (T0) was 15 minutes). In comparison with the blood before the electric potential therapy device 1 was used, it was observed that "aggregated red blood cells" had changed to "agglutinated red cells," which move.

Clumps of red blood cells (rouleaux red cells, aggregated red blood cells) are caused when the electric potential on blood cell surfaces wanes to weaken repelling force therebetween. It was observed that using the electric potential therapy device 1, however, causes polar repulsion among red-blood cells, reducing clumps of red blood cells (rouleaux red cells, aggregated red blood cells).

Third Example

Figure 21:
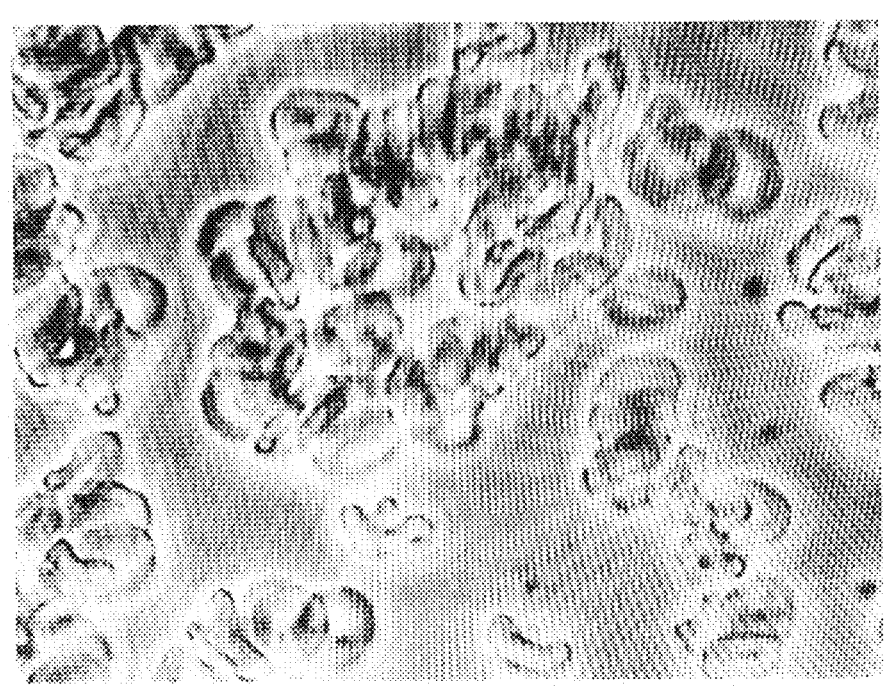
FIG. 21(*a*) is a phase contrast microscope photograph showing blood before an electric potential therapy device was used in a third example, and FIG. 21(*b*) is a phase contrast microscope photograph showing blood after the electric potential therapy device was used in the third example.
Figure 21:
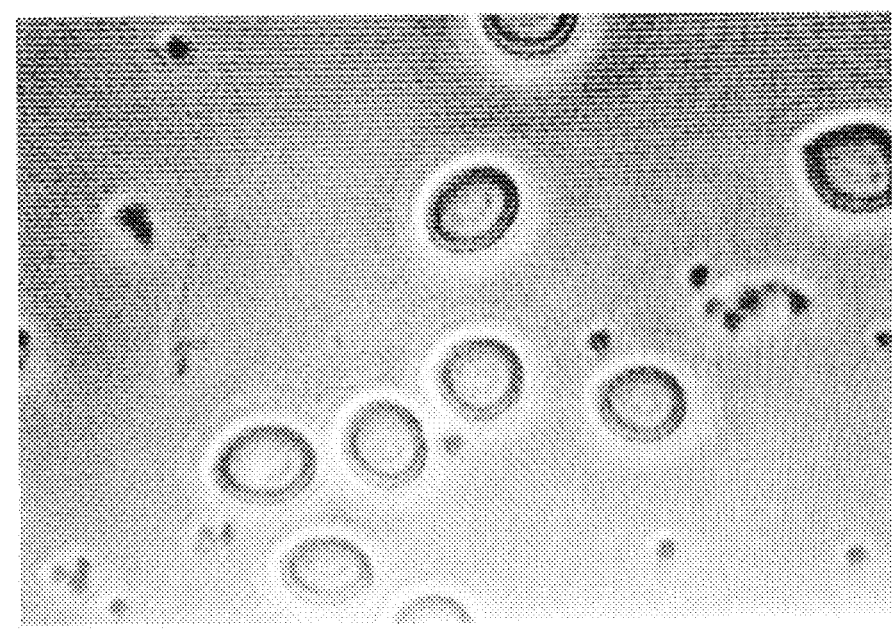

Blood was collected from a man in his 40's and observed under a phase contrast microscope. FIG. 21(*a*) shows a condition of the blood before the electric potential therapy device 1 was used on the man, and many "aggregated red blood cells" and many non-spherical "red blood cells in distorted shape" were observed. FIG. 21(*b*) shows a condition of the blood after the electric potential therapy device 1 was used on the man (the electric potential therapy device 1 was used once; the applied voltage was −1000 V, the time duration of use (T0) was 15 minutes). In comparison with the blood before the electric potential therapy device 1 was used, clumps of red blood cells (aggregated red blood cells) had apparently reduced in number. Also, although "schistocytes" were observed, their distorted shape had changed to near-circular normal shape.

Although the embodiments of the invention and modifications thereof have been described above, the invention is not limited thereto, and various changes and modifications are possible.

For example, the value of the voltage applied to the living body P is maintained constant in the above first embodiment and varies at random in the second embodiment. In a different embodiment, however, an electric potential therapy device has a first mode and a second mode. When the electric potential therapy device is in the first mode, the value of the voltage applied to the living body P is made constant, whereas when the electric potential therapy device is in the second mode, the value of the voltage applied to the living body P varies at random.

EXPLANATION OF REFERENCE NUMBERS

1, 101 electric potential therapy device
2, 102 negative voltage applying means (negative voltage applying unit)
3 electrostatic charge removing means (electrostatic charge removing unit)
4 processor (controller)
22 application electrode (first electrode)
33 removing electrode (second electrode)
P living body

What is claimed is:
1. An electric potential therapy device comprising:
a negative voltage applying unit configured to apply a negative voltage to a living body;
an electrostatic charge removing unit configured to remove electrostatic charges from inside the living body; and
a controller configured to control the negative voltage applying unit and the electrostatic charge removing unit in a predetermined therapy time in which a therapy cycle is repeated a plurality of times, the therapy cycle consisting of a first period and a second period, wherein:

the negative voltage applying unit includes a negative voltage generator that generates a negative voltage and a first electrode connected to the negative voltage generator;

the negative voltage generated by the negative voltage generator is applied to the living body through the first electrode;

the controller charges the living body to a negative potential in the first period by controlling the negative voltage applying unit to apply the negative voltage to the living body;

the controller puts the living body into a non-charged state by controlling the electrostatic charge removing unit to remove electrostatic charges from inside the living body in the second period; and the value of the voltage applied to the living body in the first period is between −600 V to −3600 V.

2. The electric potential therapy device according to claim 1, wherein:

the value of the voltage applied to the living body in the first period changes within a predetermined range at random or in a predetermined pattern.

3. The electric potential therapy device according to claim 1, wherein a time duration of the first period is 5 seconds to 30 seconds, and a time duration of the second period is 1/1000 second to 1/200 second.

4. The electric potential therapy device according to claim 1 is a kidney failure therapy device.

5. The electric potential therapy device according to claim 1 is an oxidative stress relieving device.

6. The electric potential therapy device according to claim 1, wherein:

the controller outputs an application signal and a removing signal;

the negative voltage applying unit applies the negative voltage to the living body when receiving the application signal from the controller;

the electrostatic charge removing unit removes electrostatic charges from the living body when receiving the removing signal from the controller; and the controller outputs the application signal to the negative voltage applying unit during the entire therapy period and the removing signal to the electrostatic charge removing unit in the second period.

7. The electric potential therapy device according to claim 1, wherein:

the controller outputs an application signal and a removing signal;

the negative voltage applying unit applies the negative voltage to the living body when receiving the application signal from the controller;

the electrostatic charge removing unit removes electrostatic charges from the living body when receiving the removing signal from the controller; and the controller outputs the application signal to the negative voltage applying unit in the first period and the removing signal to the electrostatic charge removing unit in the second period.

8. The electric potential therapy device according to claim 1, wherein:

the electrostatic charge removing unit includes electrostatic charge consuming member, a switch, and a second electrode;

the controller turns OFF the switch in the first period and turns ON the switch in the second period; and when the switch is turned ON, then the second electrode is electrically connected to the charge consuming member via the switch, letting the electrostatic charges flow from the living body to the electrostatic charge consuming member via the second electrode and the switch and be consumed by the electrostatic charge consuming member.

9. The electric potential therapy device according to claim 1, wherein the electrostatic charge removing unit includes a switch and a second electrode;

the controller turns OFF the switch in the first period and turns ON the switch in the second period; and when the switch is turned ON, then the second electrode is electrically connected to the earth ground through the switch, resulting in the electrostatic charge being removed from the living body and discharged to the earth ground via the second electrode and the switch.

10. An electric potential therapy device comprising:

a negative voltage applying unit configured to apply a negative voltage to a living body;

an electrostatic charge removing unit configured to remove electrostatic charges from inside the living body; and a controller configured to control the negative voltage applying unit and the electrostatic charge removing unit in a predetermined therapy time in which a therapy cycle is repeated a plurality of times, the therapy cycle consisting of a first period and a second period, wherein:

the negative voltage applying unit includes a negative voltage generator that generates a negative voltage and a first electrode connected to the negative voltage generator;

the negative voltage generated by the negative voltage generator is applied to the living body through the first electrode;

the controller charges the living body to a negative potential in the first period by controlling the negative voltage applying unit to apply the negative voltage to the living body;

the controller puts the living body into a non-charged state by controlling the electrostatic charge removing unit to remove electrostatic charges from inside the living body in the second period;

a time duration of the first period is 5 seconds to 30 seconds; and a time duration of the second period is 1/1000 second to 1/200 second.

* * * * *